United States Patent [19]

Andreiko

[11] Patent Number: 5,088,923
[45] Date of Patent: Feb. 18, 1992

[54] ALLOY FOR ATTACHING ORTHODONTIC BRACKET TO ORTHODONTIC PAD

[75] Inventor: Craig A. Andreiko, Alta Loma, Calif.

[73] Assignee: Ormco Corporation, Glendora, Calif.

[21] Appl. No.: 467,161

[22] Filed: Jan. 19, 1990

[51] Int. Cl.⁵ .............................................. A61C 7/00
[52] U.S. Cl. ......................................................... 433/9
[58] Field of Search ........................................ 433/8, 9

[56] References Cited

U.S. PATENT DOCUMENTS

| 4,256,455 | 3/1981 | Förster | 433/9 X |
| 4,460,336 | 7/1984 | Smith et al. | 433/9 |
| 4,527,979 | 7/1985 | McLean et al. | 433/9 X |
| 4,551,094 | 11/1985 | Kesling | 433/8 |

FOREIGN PATENT DOCUMENTS 242171 1/1987 German Democratic Rep. .... 433/9

Primary Examiner—Robert P. Swiatek
Attorney, Agent, or Firm—Ellsworth R. Roston; Charles H. Schwartz

[57] ABSTRACT

First and second members are constructed to be disposed in an individual's body without adversely affecting the functioning of the individual's body. The first and second members may be illustratively an orthodontic bracket and an orthodontic pad. An amorphous alloy is disposed between or adjacent to the first and second members in a thin layer (e.g. three thousandths of an inch (0.003")) and is bonded, as by brazing, to the first and second members. The alloy is provided with properties of not affecting the functioning of the individual's body adversely. The alloy preferably has eutectic properties and has properties of being ductile and corrosion resistant. The alloy is preferably a metallic glass in which the primary element may be palladium. The alloy may consist of palladium, nickel and silicon. The composition of the alloy is preferably as follows:

| Element | Approximate Percentage |
|---------|------------------------|
| Palladium | Ninety percent (90%) |
| Nickel | Four Percent (4%) |
| Silicon | Six Percent (6%) |

The alloy is not dense so that a minimal amount of material has to be used to bond the first and second members. The alloy provides a stronger bond to the first and second members than the alloys of the prior art.

20 Claims, 1 Drawing Sheet

ALLOY FOR ATTACHING ORTHODONTIC BRACKET TO ORTHODONTIC PAD

This invention relates to orthodontic braces. More particularly, the invention relates to orthodontic braces which include a bracket assembly and an arch wire in which the bracket assembly include a pad and a bracket bonded by an alloy of superior properties.

When the teeth in a patient's mouth are displaced from an even or uniform disposition, such displacements tend to produce problems over an extended period of time. For example, such displacements may produce problems in the patient's gums. These problems may cause the retention of teeth by the patient's gums to become weakened so that the teeth become loose in the patient's mouth. The problem may become so aggravated that the teeth may eventually have to be removed from the patient's mouth.

To prevent the conditions in a patient's mouth from deteriorating, orthodontists often attempt to reset the positions of the teeth in the patient's mouth. The orthodontists do this by attaching braces to the patient's teeth and by gradually adjusting the forces applied by the braces to the teeth. These forces act against the teeth in the patient's mouth to move the teeth gradually toward the positions desired by the orthodontist.

The braces are generally formed by bracket assemblies (each formed from a support member and a pad) and an arch wire supported in a groove in each of the support members. The support member in each bracket assembly is adhered to an individual tooth by the pad, which is attached to the support member. The arch wire extends between the brackets on adjacent teeth and applies a force to the teeth to move the teeth toward their desired positions. As the arch wire moves the teeth toward the positions predetermined by the patient's orthodontist, the orthodontist can adjust the brace to vary the forces imposed by the arch wire on the teeth.

The support member in each bracket may be made from a suitable material such as stainless steel, and the pad is preferably in the form of a mesh made from a suitable material such as stainless steel. Stainless steel is desirable because it will not corrode in the patient's mouth. The support member and the pad in each bracket are adhered by a suitable alloy.

The alloys now in use for adhering the support member and the pad have certain inherent disadvantages. One disadvantage is that the alloy tends to corrode in the patient's mouth. This is not desirable from the standpoint of the patient's health and it is also not aesthetic. Another disadvantage is that the alloy does not form as strong a bond between the support member and the pad as the orthodontist often desires. Further disadvantages are that the alloy is dense and is expensive. Because of this, even though the alloy is applied in a thin layer to the support member and the pad, the cost of the alloy adds materially to the cost of the brace. Still another disadvantage is that it is difficult to apply the alloy in a substantially uniform layer to the support member and the pad.

The disadvantages discussed in the previous paragraph have been known for some time. A considerable effort has been made, and significant amounts of money have been expended, to overcome these disadvantages. In spite of such efforts and expenditure of money, alloys continue to be used with the disadvantages discussed above.

In one embodiment of the invention, first and second members are constructed to be disposed in an individual's body without adversely affecting the functioning of the individual's body. The first and second members may be illustratively an orthodontic bracket and an orthodontic pad.

An amorphous alloy is disposed between or adjacent to the first and second members in a thin layer (e.g. three thousandths of an inch (0.003")) and is bonded, as by brazing, to the first and second members. The alloy is provided with properties of not affecting the functioning of the individual's body adversely. The alloy has eutectic properties and has properties of being ductile and corrosion resistant.

The alloy is preferably a metallic glass in which the primary element may be palladium. The alloy may consist of palladium, nickel and silicon. The composition of the alloy is preferably as follows:

| Element | Approximate Percentage |
| --- | --- |
| Palladium | Ninety percent (90%) |
| Nickel | Four Percent (4%) |
| Silicon | Six Percent (6%) |

The alloy is not dense so that a minimal amount of material has to be used to bond the first and second members. The alloy provides a stronger bond to the first and second members than the alloys of the prior art.

Figure 1:
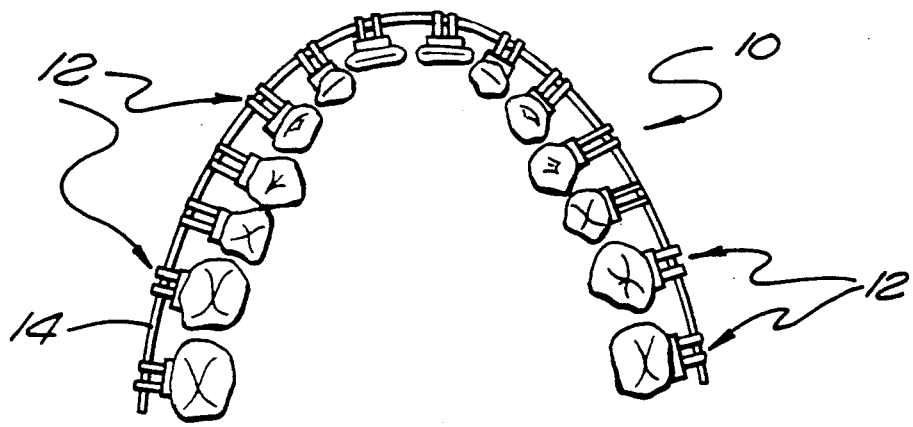
FIG. 1 is a plan view schematically of a set of teeth in a patient's mouth and a brace supported by the teeth to adjust the positioning of the teeth, the brace including a plurality of brackets and an arch wire.
Figure 2:
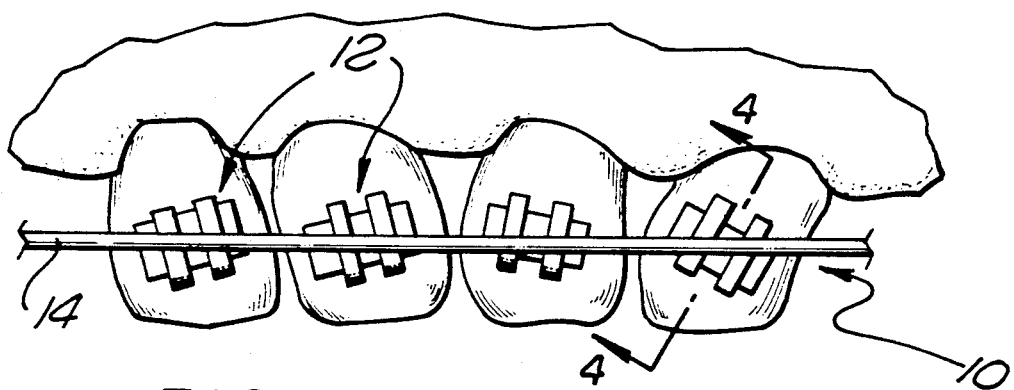
FIG. 2 is an enlarged fragmentary elevational view of some of the teeth and a portion of the brace shown in FIG. 1.
Figure 3:
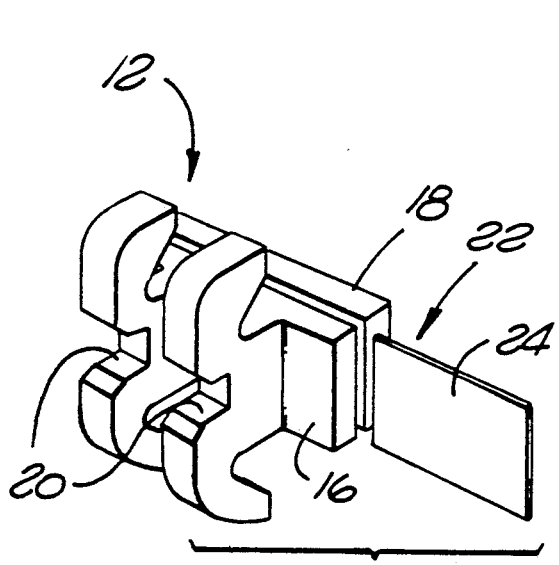
FIG. 3 is an enlarged exploded perspective view of one of the bracket assemblies shown in FIGS. 1 and 2 before different elements in the assembly have been adhered to each other.
Figure 4:
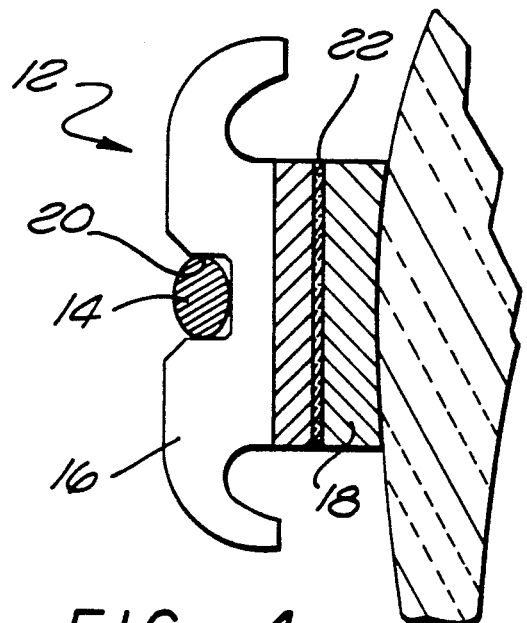
FIG. 4 is an enlarged sectional view of the bracket assembly shown in FIG. 3 after the different elements in the assembly have been adhered to each other.

In one embodiment of the invention, a brace generally indicated at 10 is provided. The brace 10 includes a plurality of bracket assemblies generally indicated at 12 and an arch wire 14. Each bracket assembly 12 includes a support member 16 and a pad 18. The support member 16 and the pad 18 are adapted to be made from a suitable material such as stainless steel so as to be impervious to the acids in an individual's body. The support member 16 and the pad 18 may be provided with a conventional construction.

The support member 16 may be provided with a groove 20 which is shaped to receive the arch wire 14. The support member 16 is attached to one surface of the pad 18 as by a thin layer of an alloy 22. The other surface of the pad 18 is adapted to be bonded to a patient's tooth. By attaching a different bracket 12 to each individual tooth and by controlling the depth, angle and position of the groove 20 in each support member 16, an arch wire 14 disposed in the groove 20 in the different support members can be provided with characteristics to impose a force on the patient's teeth to move the teeth to a desired configuration in the patient's mouth.

The alloy 22 is preferably made from an amorphous layer. This is desirable because the grains of an amorphous material are small. This allows the layer of the alloy 22 between the support member 16 and the pad 18 to be thin and substantially uniform in thickness even when the alloy is brazed to the support member and the pad. This alloys the alloy to be ductile, thereby facilitating the bond to the support member and the pad.

The alloy is preferably made from a metallic glass. Preferably the metallic glass has eutectic properties to minimize the temperature at which the alloy is melted to bond the support member 16 and the brace 18. This metallic alloy may be formed from a combination of palladium, nickel and silicon, palladium being the primary element in the combination. Preferably the alloy may have the following composition:

| Element | Approximate Percentage |
| --- | --- |
| Palladium | Approximately Ninety percent (90%) |
| Nickel | Approximately Four Percent (4%) |
| Silicon | Approximately Six Percent (6%) |

The alloy 22 may be formed in thin strips or segments 24 approximately six thousandths of an inch (0.006") thick. One of the strips or segments 24 may be disposed adjacent a support member 16 and a pad 18 and may be heated to a temperature of approximately 1750° F.–1900° F. This is above the melting temperature of the alloy, this melting temperature being approximately 1625° F. When the strip or segment 24 is melted, it flows in liquidus form by capillary action between the support member 16 and the pad 18 and forms a bonding layer approximately three thousandths of an inch (0.003") thick.

The brace 10 constituting this invention has certain important advantages. In this brace, the support member 16 and the pad 18 are bonded to each other by the alloy 22 more firmly than in the prior art. Furthermore, none of the elements in the brace, including the alloy 22, will tarnish. In the braces of the prior art, the alloy has tarnished.

The alloy 22 of this invention does not tarnish as do the alloys of the prior art. This is particularly important when the alloy is used in orthodontic braces because tarnishing distracts from the aesthethic appearance of the brace. The alloy 22 of this invention is also less dense than the alloys of the prior art. This causes the amount of material used in the alloy 22 of this invention to bond the support member and the pad to be considerably less than in the alloys of the prior art. This difference may be as high as seventy percent (70%). This is of particular importance since the alloy of this invention uses a precious metal (palladium) and the alloys of the prior art use a precious metal such as silver. As will be appreciated, precious metals such as palladium and silver are quite expensive. Applicant has found that the cost of bonding a support member 16 and a pad 18 by using the alloy 22 of this invention is approximately sixty percent (60%) less than by using the alloys of the prior art.

The invention has been described with particular reference to an orthodontic brace. However, it will be appreciated that the alloy 22 can be used to bond other members which can be disposed in a patient's body. For example, the alloy 22 of this invention can be used to bond members in heart valves without departing from the scope of the invention.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination in an orthodontic bracket,
an orthodontic support member,
an orthodontic pad, and
an amorphous alloy disposed in a thin layer between the pad and the support member and bonding the support member and the pad, the amorphous alloy having eutectic properties when heated to at least the melting temperature and having properties, when melted, of flowing in liquidus form by capillary action between the support member and the pad,
the alloy being disposed between the support member and the pad in a layer of approximately three thousandths of an inch (0.003").

2. In a combination as set forth in claim 1,
the amorphous alloy having properties of not tarnishing when exposed to saliva in a patient's mouth.

3. In combination in an orthodontic bracket,
an orthodontic support member,
an orthodontic pad, and
an amorphous alloy disposed in a thin layer between the pad and the support member and bonding the support member and the pad,
the alloy being disposed between the support member and the pad in a layer of approximately three thousandths of an inch (0.003"),
the alloy being made primarily from palladium.

4. In combination in an orthodontic bracket,
an orthodontic support member,
an orthodontic pad, and
a metallic glass alloy disposed between the orthodontic support member and the orthodontic pad in a thin layer and bonding the orthodontic support member to the orthodontic pad.

5. In a combination as set forth in claim 4,
the metallic glass alloy primarily including palladium.

6. In a combination as set forth in claim 5,
the metallic glass alloy being formed from a combination of palladium, silicon and nickel.

7. In combination in an orthodontic bracket,
an orthodontic support member,
an orthodontic pad, and
a metallic glass alloy primarily including palladium and having eutectic properties, the metallic glass alloy being disposed between the orthodontic support member and the orthodontic pad and being bonded to the orthodontic support member and the orthodontic pad.

8. In a combination as set forth in claim 7,
the metallic glass alloy being formed from a combination of palladium, silicon and nickel.

9. In a combination as set forth in claim 8,
the metallic glass alloy being disposed between the orthodontic support member and the orthodontic pad in a substantially uniform layer substantially three thousandths of an inch (0.003") thick.

10. In a combination as set forth in claim 9, the metallic glass being made from a combination of palladium, silicon and nickel with eutectic properties.

11. In combination in an orthodontic bracket,
an orthodontic support member,
an orthodontic pad, and
a layer of an alloy consisting of the following elements in the following approximately percentages:

| Element | Approximate Percentage |
| --- | --- |
| Palladium | Ninety percent (90%) |
| Nickel | Four Percent (4%) |
| Silicon | Six Percent (6%). |

12. In a combination as recited in claim 11,
the layer of the alloy having a substantially uniform thickness of approximately three thousandths of an inch (0.003").

13. In combination for use in an individual's body without tarnishing and without adversely affecting the functioning of the individual's body,
- a first member constructed to be disposed in the individual's body without adversely affecting the functioning of the individual's body,
- a second member constructed to be disposed in the individual's body without adversely affecting the functioning of the individual's body,
- an amorphous alloy disposed between the first and second members in a thin layer and bonded to the first and second members and having properties of not affecting the functioning of the individual's body,
- the amorphous layer constituting an amorphous glass alloy.

14. In a combination as set forth in claim 13,
the first and second members and the amorphous layer having properties of being ductile and corrosion resistant and of becoming disposed between the first and second members by capillary action.

15. In a combination as set forth in claim 14,
the alloy primarily consisting of palladium.

16. In combination for use in an individual's body without tarnishing and without adversely affecting the functioning of the individual's body,
- a first member constructed to be disposed in the individual's body without adversely affecting the functioning of the individual's body,
- a second member constructed to be disposed in the individual's body without adversely affecting the functioning of the individual's body, and
- a metallic glass alloy disposed between the first and second members in a thin layer and brazed to the first and second members.

17. In a combination as set forth in claim 16,
the metallic glass alloy having properties of being ductile and corrosion resistant and of becoming disposed between the first and second members by capillary action.

18. In a combination as set forth in claim 16,
the metallic glass alloy primarily consisting of palladium.

19. In a combination as set forth in claim 18,
the metallic glass alloy consisting of palladium, nickel and silver.

20. In a combination as set forth in claim 16,
the alloy consisting of the following elements in the following approximate percentage:

| Element | Approximate Percentage |
| --- | --- |
| Palladium | Approximately Ninety percent (90%) |
| Nickel | Approximately Four Percent (4%) |
| Silicon | Approximately Six Percent (6%). |

* * * * *